(12) United States Patent
Herrera

(10) Patent No.: US 8,968,239 B2
(45) Date of Patent: Mar. 3, 2015

(54) CATHETER DEVICE FOR THE DYNAMIC REGULATION OF THE VENOUS RETURN TO THE HEART FOR THE TREATMENT OF PATIENTS WITH HEART FAILURE

(76) Inventor: Jose E. Herrera, Porlamar (VE)

( * ) Notice: Subject to any disclaimer, the term of this patent is extended or adjusted under 35 U.S.C. 154(b) by 389 days.

(21) Appl. No.: 12/801,813

(22) Filed: Jun. 28, 2010

(65) Prior Publication Data
US 2010/0331876 A1 Dec. 30, 2010

Related U.S. Application Data

(63) Continuation-in-part of application No. 12/202,617, filed on Sep. 2, 2008, now abandoned.

(51) Int. Cl.
*A61M 31/00* (2006.01)
*A61M 37/00* (2006.01)
(Continued)

(52) U.S. Cl.
CPC ........... *A61M 25/04* (2013.01); *A61M 25/1002* (2013.01); *A61B 17/12036* (2013.01); *A61M 2025/0096* (2013.01); *A61M 2025/1052* (2013.01); *A61M 2025/1086* (2013.01)
USPC ................ 604/103.08; 604/96.01; 604/103.03

(58) Field of Classification Search
USPC ............................ 604/103.01, 101.01–101.05
See application file for complete search history.

(56) References Cited

U.S. PATENT DOCUMENTS 4,798,588 A 1/1989 Aillon
5,250,070 A 10/1993 Parodi (Continued)

FOREIGN PATENT DOCUMENTS

WO WO9951286 A1 10/1999
WO WO2007014028 A1 2/2007

OTHER PUBLICATIONS

International Search Report for Application No. PCT/IB 2009/052506, Jun. 4, 2010, 6 pages, Austrian Patent Office, Vienna, Austria.

(Continued)

*Primary Examiner* — Rebecca E Eisenberg
(74) *Attorney, Agent, or Firm* — Ference & Associates LLC

(57) ABSTRACT

This invention relates to a method that comprises the introduction of a catheter via left subclavian vein, advancing into the right atrium and then positioning it in the inferior vena cava, just at the cava-diaphragm junction, where it is anchored at its extreme; and thereafter an external inflation of a balloon positioned in said catheter takes place through a physiological solution to reach a diameter corresponding to half the diameter of the inferior vena cava, resulting in hemi-occlusion in the expiration phase (breath-out) and total occlusion for a short period during the inspiration phase (breath-in), regulating (normalizing) the venous return and decreasing the cardiac volume overload, as a treatment for heart failure. The invention also comprises hydromechanics devices to normalize the venous return in the circulatory system. Said venous return is increased in 90% of patients with heart failure. In particular, it refers to a combined catheter with an inflatable balloon, producing said balloon a cyclical occlusion of the inferior vena cava (IVC). The said balloon is adaptable to the area of its location in the inferior vena cava, proximal to the right atrium (RA), which comprises of means for its fixation within said vein, as well as the capacity of modifying the volume in response to the requirements of the patient. This device is implanted for an extended period of more than three months. The final objective is to treat and stop the progression of heart failure.

6 Claims, 8 Drawing Sheets

(51) Int. Cl.

| | | |
|---|---|---|
| *A61M 29/00* | (2006.01) | |
| *A61M 25/04* | (2006.01) | |
| *A61M 25/10* | (2013.01) | |
| *A61B 17/12* | (2006.01) | |
| *A61M 25/00* | (2006.01) | |

(56) References Cited

U.S. PATENT DOCUMENTS

| | | | | |
|---|---|---|---|---|
| 5,545,132 | A | 8/1996 | Fagan et al. | |
| 2003/0009095 | A1* | 1/2003 | Skarda | 600/374 |
| 2003/0208232 | A1 | 11/2003 | Blaeser et al. | |
| 2004/0215228 | A1 | 10/2004 | Simpson et al. | |
| 2004/0225318 | A1 | 11/2004 | Eidenschink et al. | |
| 2006/0009827 | A1 | 1/2006 | Kurth et al. | |
| 2006/0064059 | A1 | 3/2006 | Gelfand et al. | |
| 2006/0074399 | A1 | 4/2006 | Bates | |
| 2008/0051707 | A1* | 2/2008 | Phan et al. | 604/108 |
| 2008/0086083 | A1* | 4/2008 | Towler | 604/103.06 |
| 2009/0227949 | A1* | 9/2009 | Knapp et al. | 604/103.02 |

OTHER PUBLICATIONS

Supplementary European Search Report for Application No. EP09811175, Dec. 2, 2011, 2 pages, Berlin, Germany.

Belenkov, Yu. N. et al., Section 7, Adjuvant treatment of CHF (chronic heart failure), in Principles of Good Treatment Heart Failure (2001), pp. 130-163 (in Russian) available at Internet page: http://alt-lib.ru/wp-content/uploads/2012/%D0%91%D0%B5%D0%BB%D0%B5%D0%BD%D0%BA%D0%BE%D0%B2-%D0%AE.%D0%9D.-%D0%9C%D0%B0%D1%80%D0%B5%D0%B5%D0%B2-%D0%92.%D0%AE.-%D0%9F%D1%80%D0%B8%D0%BD%D1%86%D0%B8%D0%BF%D1%8B-%D1%80%D0%B0%D1%86%D0%B8%D0%BE%D0%BD%D0%B0%D0%BB%D1%8C%D0%BD%D0%BE%D0%B3%D0%BE-%D0%BB%D0%B5%D1%87%D0%BD%D0%B8%D1%8F-%D1%81%D0%B5%D1%80%D0%B4%D0%B5%D1%87%D0%BD%D0%BE%D0%B9-%D0%BD%D0%B5%D0%B4%D0%BE%D1%81%D1%82%D0%B0%D1%82%D0%BE%D1%87%D0%BD%D0%BE%D1%81%D1%82%D0%B8-2000.pdf last accessed Feb. 7, 2014.

Inquiry of the Examiner on the Merits, Russian Office Action, English Translation for Application No. 2011112308/14 (018179), Feb. 26, 2013, 5 pages, Federal Intellectual Property Service, Federal State Budget Agency, Federal Institute of Industrial Property (FIPS), Moscow, Russia.

Belenkov, Yu. N. et al., Section 7, Adjuvant treatment of CHF (chronic heart failure), in Principles of Good Treatment Heart Failure (2000), pp. 130-163 (in Russian) available at Internet page: http://alt-lib.ru/wp-content/uploads/2012/%D0%91%D0%B5%D0%BB%D0%B5%D0%BD%D0%BA%D0%BE%D0%B2-%D0%AE.%D0%9D.-%D0%9C%D0%B0%D1%80%D0%B5%D0%B5%D0%B2-%D0%92.%D0%AE.-%D0%9F%D1%80%D0%B8%D0%BD%D1%86%D0%B8%D0%BF%D1%8B-%D1%80%D0%B0%D1%86%D0%B8%D0%BE%D0%BD%D0%B0%D0%BB%D1%8C%D0%BD%D0%BE%D0%B3%D0%BE-%D0%BB%D0%B5%D1%87%D0%BD%D0%B8%D1%8F-%D1%81%D0%B5%D1%80%D0%B4%D0%B5%D1%87%D0%BD%D0%BE%D0%B9-%D0%BD%D0%B5%D0%B4%D0%BE%D1%81%D1%82%D0%B0%D1%82%D0%BE%D1%87%D0%BD%D0%BE%D1%81%D1%82%D0%B8-2000.pdf last accessed Feb. 7, 2014.

* cited by examiner

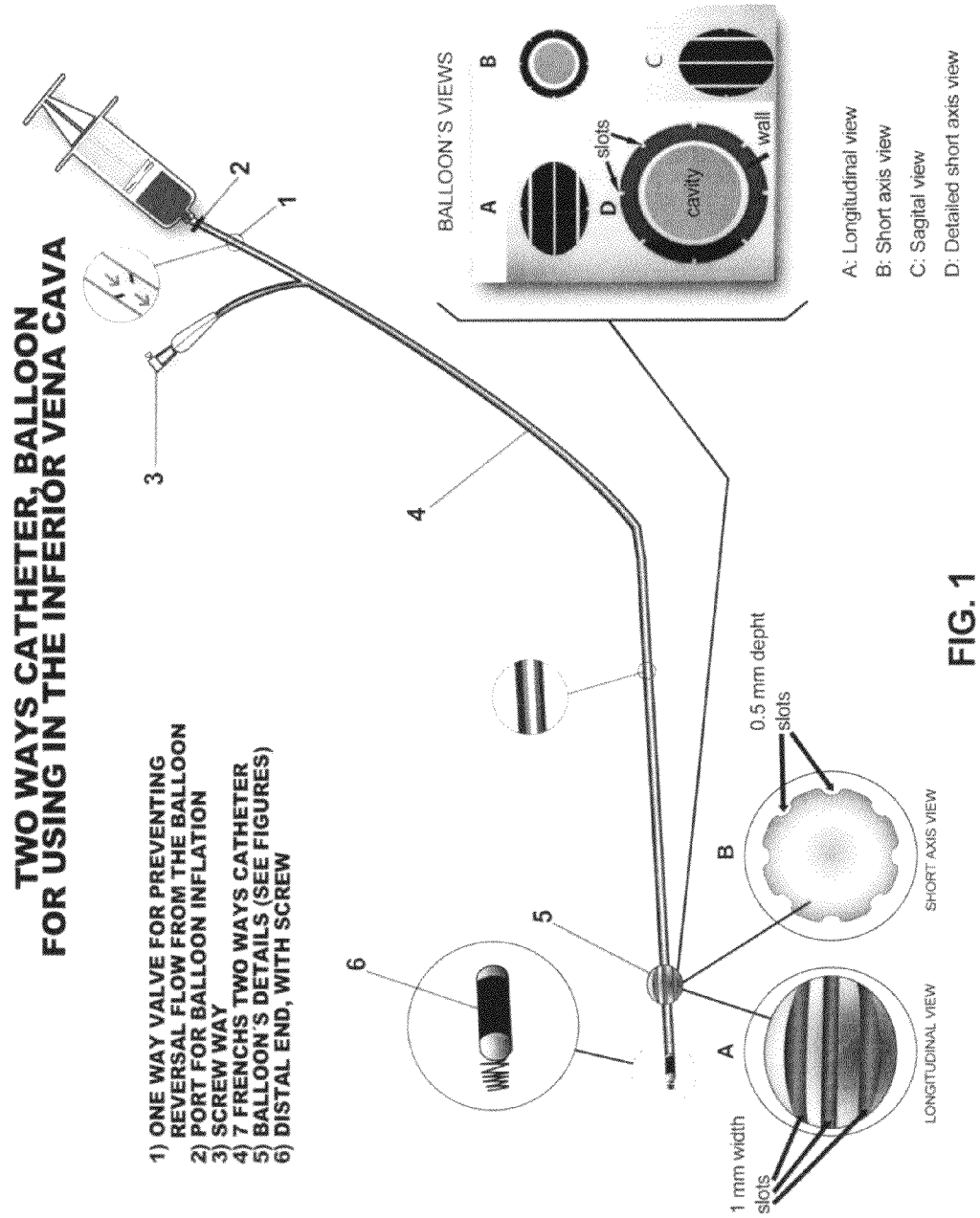

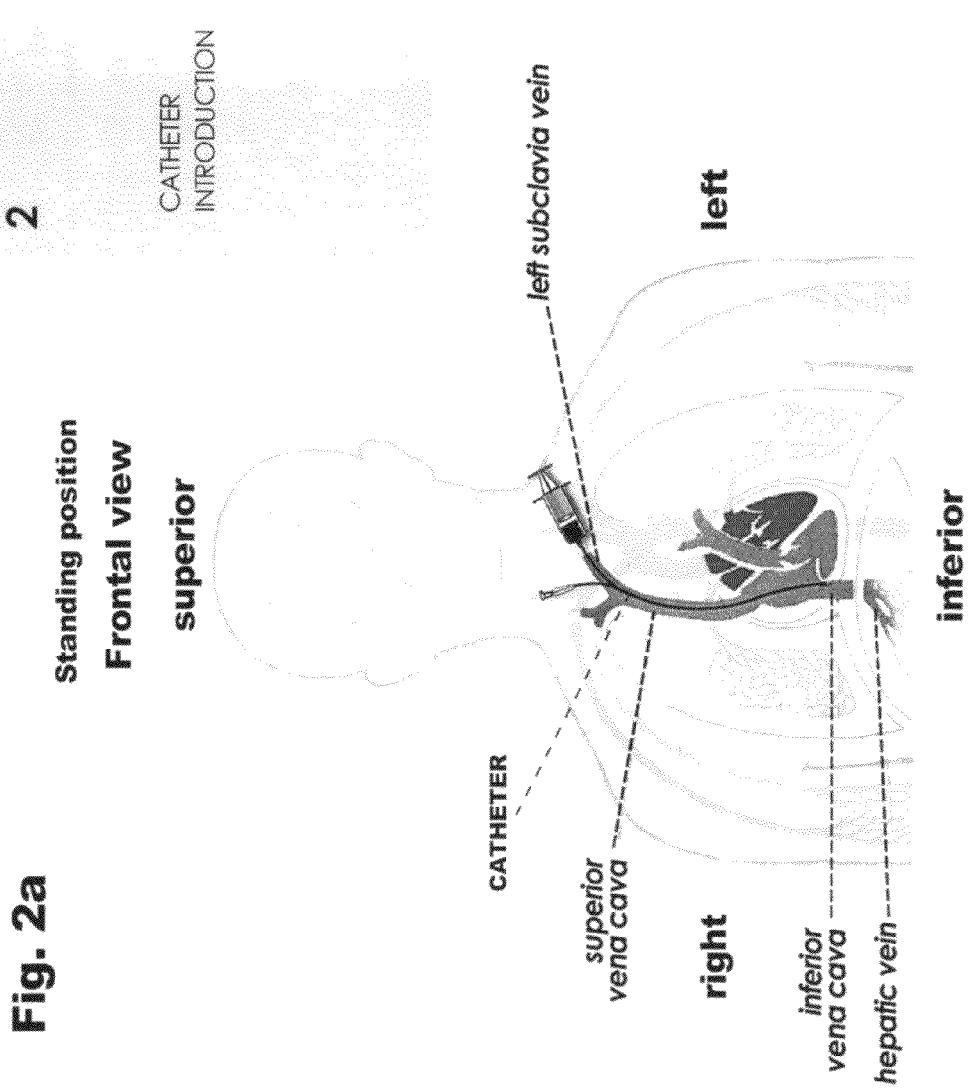

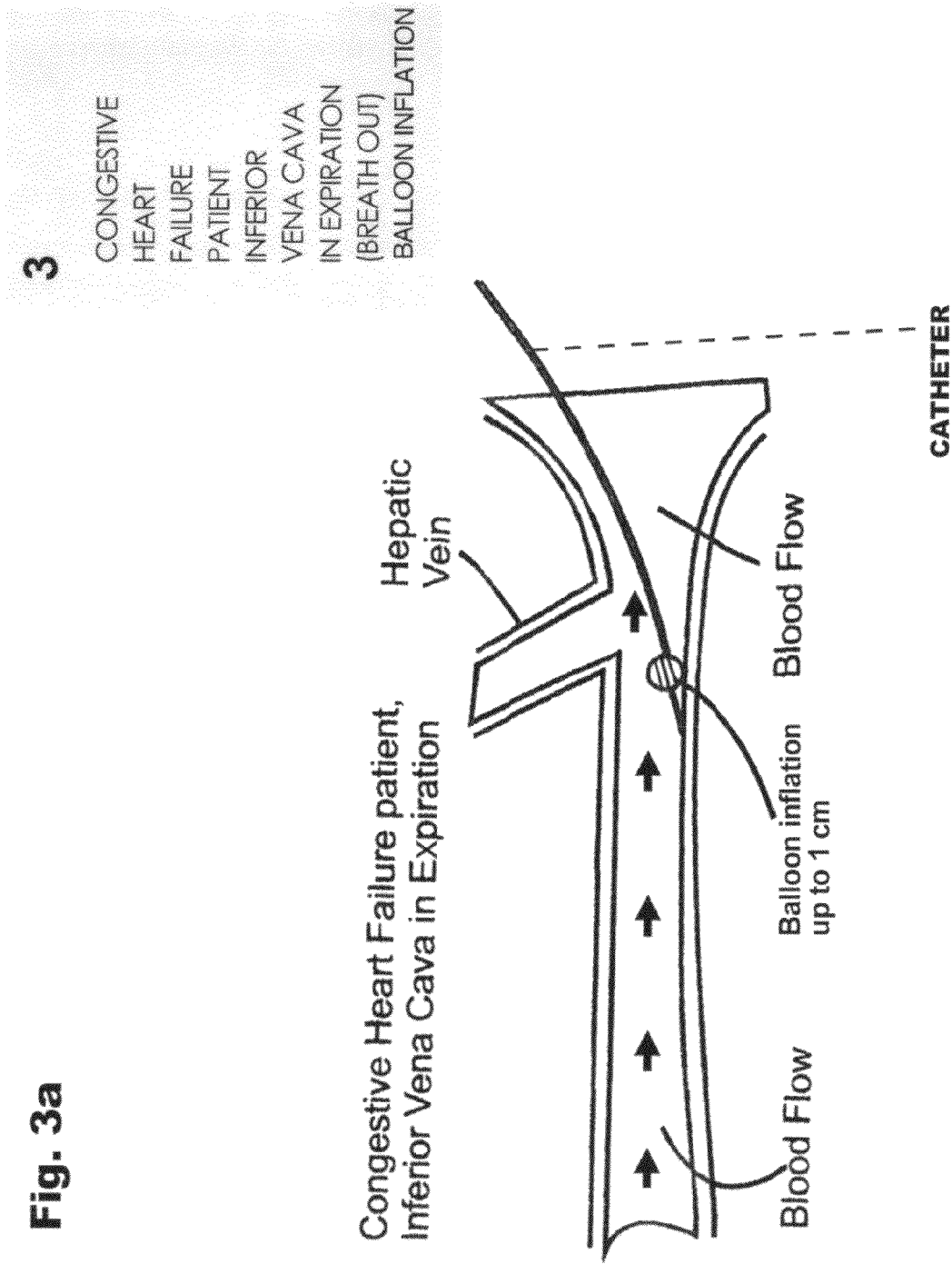

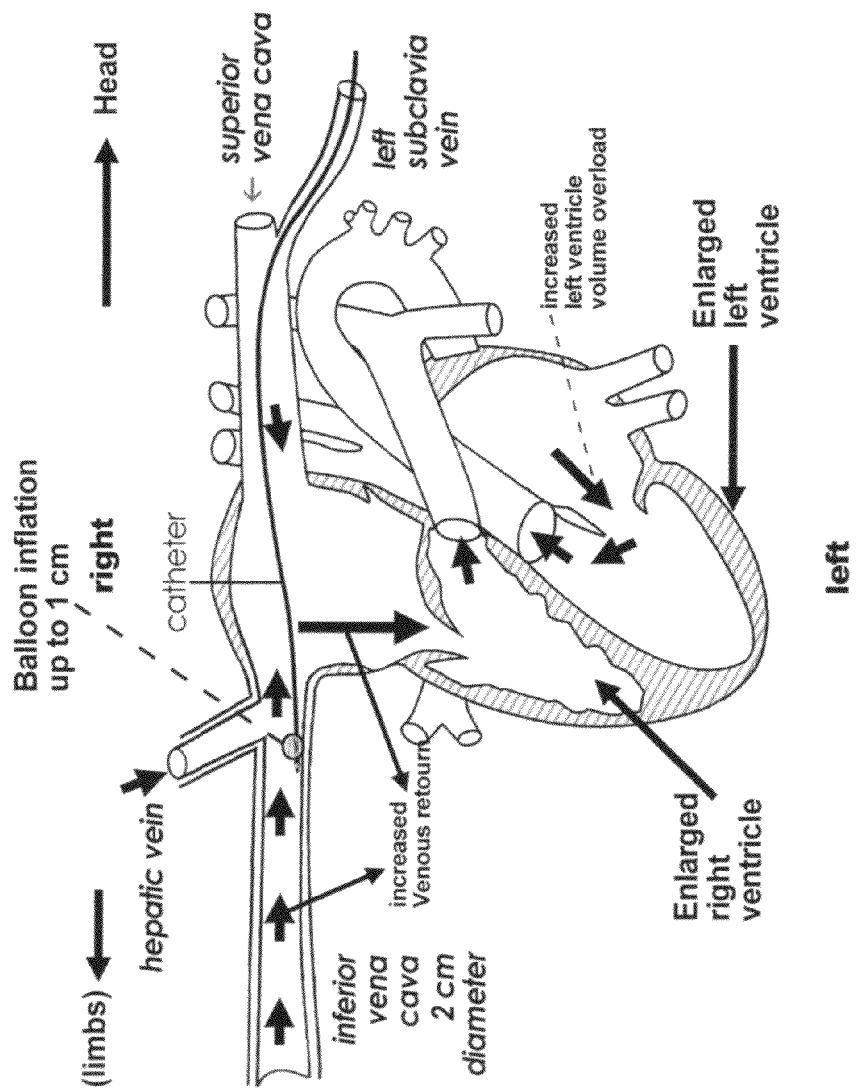

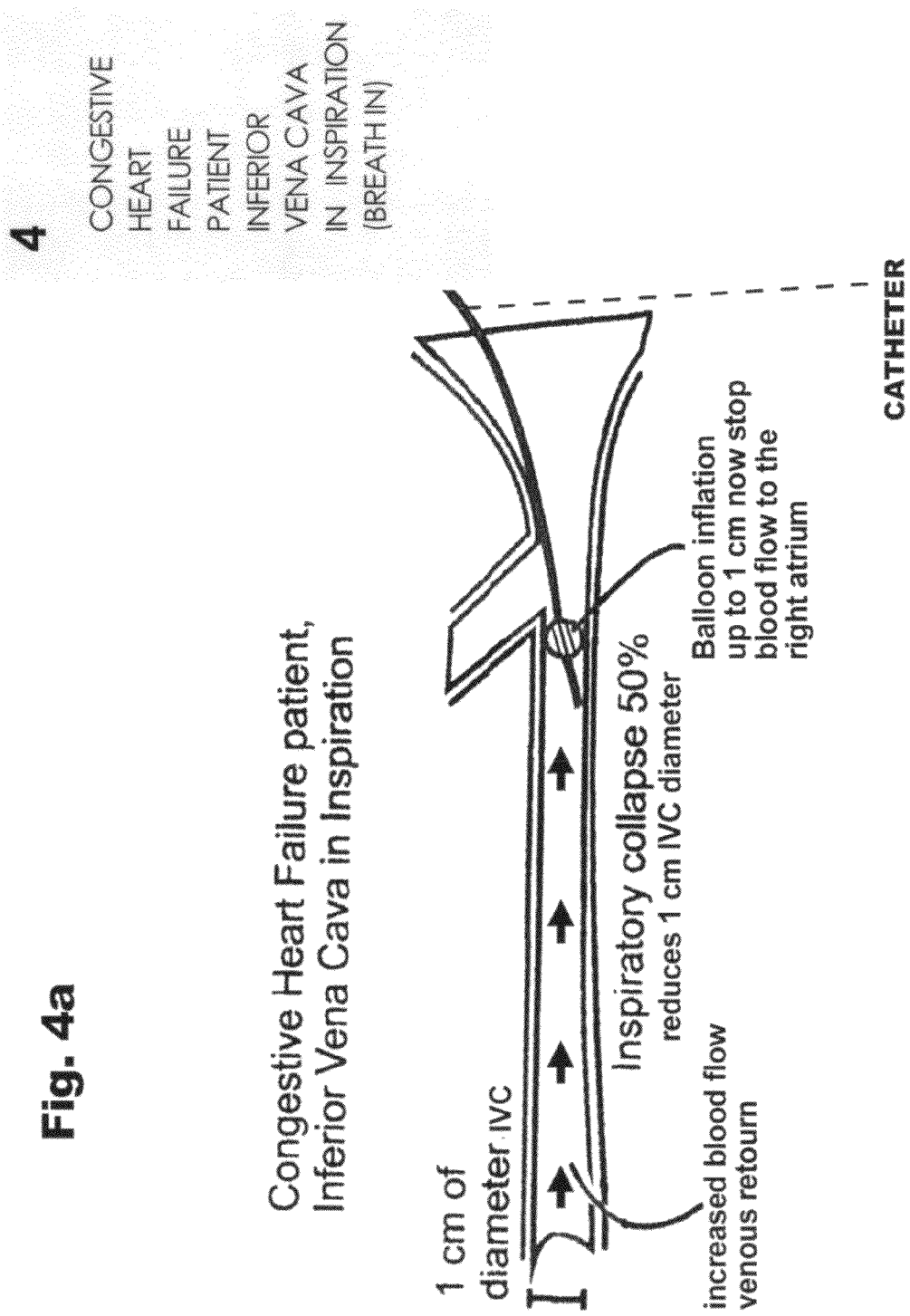

CATHETER DEVICE FOR THE DYNAMIC REGULATION OF THE VENOUS RETURN TO THE HEART FOR THE TREATMENT OF PATIENTS WITH HEART FAILURE

This is a continuation-in-part of application Ser. No. 12/202,617, filed Sep. 2, 2008 now abandoned.

BACKGROUND OF THE INVENTION

It has been known within the field of the specialty that heart failure is a result of the increase of the venous return which causes volume overload and severe pulmonary congestion; so that the decrease of venous return (normalization) is crucial in the improvements of the symptoms of said pulmonary congestion and heart failure. In early attempts to solve the problem, bloodletting and tourniquet in the lower extremities were used as a mean to normalize venous return, to improve the pulmonary congestion.

In later years, the use of mercurial diuretics started, then stronger ASA diuretics, furosemide and bumetanide helped to rapidly decrease the venous return, with improvements of the heart failure symptoms; however, there were deleterious effects on the renal function, such as hydro-electrolytic disorders and renal damages.

The persistence of the problem of the increased venous return led to the use of nitride and nitrates, which produce a venous dilatation, causing a reduction on the venous return, improving the symptoms for a short period of time; but the inherent intolerance in this type of medication causes the loss of the effect in a few months, with the additional inconvenience of associated headaches as side effects, as it was observed in a large percentage of patients, resulting risky the use of these medicines during extended periods of time.

After the introduction of receptor blockers of aldosterone (spironolactona), hydro saline retention was minimized, as well as venous return; however, the receptor blockers produced serious side effects.

Later on, a new pharmacological alternative was introduced in the form of drugs that block the formation of angiotensin, which produced the decrease of venous return, improving the quality of life of a patient with heart failure.

Subsequently, the use of beta blockers of the last generation type (carvediol) was advocated, and the same produced significant benefits in patients with heart failure, being a treatment choice for a high number of patients with heart failure.

With the advent of receptor blockers (V1-V2) of the neurohormonal arginine-vasopressin axis (type Tolvaptan, Conivaptan), a reducer of corporal water, decrease of venous return and improvement of pulmonary congestion is achieved for a very short period of time and at an extremely high price.

The proposal to use stem cells for the treatment of heart failure was assessed at the Annual Meeting of The American Heart Association 2007. It was considered then that this technique caused little improvement in the ejection fraction of the left ventricle; and better results are obtained only when the venous return is diminished through diuretic administration.

There is no similar method to that described in this invention to treat and improve heart failure. At device level, there are only inflatable balloons for temporary use during An invasive procedure as used in US Patent No. 2003/0208232 to Blaeser et al. (Blaeser) and in US Patent No. 2006/0074399 to Bates (Bates).

It is evident that effective management of the venous return is very important in improving the left ventricle function.

Lastly, in those extreme cases where known medical therapeutic measures fail, mechanical methods are used to normalize the venous return via extraction of corporal water, as the dialysis and ultra-filtration, which although they enable good effects in the symptoms of a congestive heart failure, this is for a short period; and the body water comeback to a state of increased venous return, reappearing the symptoms of pulmonary congestion and low cardiac output.

Objectives of the Invention

One of the objectives of the invention is to solve in efficient and effective way the above outline problems through a method of regularization of the venous return by means of hydraulic devices, in patients suffering congestive heart failure.

Another objective of the invention is to provide said regularization, a device that includes a two-way catheter carrying an inflatable balloon, adjustable in volume comprising of several external slots, so that in case of prolonged total occlusion of the inferior vena cava (laughing, coughing), these will allow the passage of venous return, as an alleviating channel to avoid cardio-circulatory collapse. Said balloon is filled from the outside, to the required setting, with a saline solution, through which an occlusion of the inferior vena cave is formed during the inspiration phase (breath in.)

An additional objective of the invention, once placed and anchored and inflated the catheter/balloon in the proximal portion of the inferior vena cava, is to produce an instantaneous dynamic cyclic occlusion depending on the respiratory phases, thereby obtaining the normalization of the flow running from the inferior vena cava toward the right atrium (RA.)

DESCRIPTION OF THE INVENTION

The present invention is intended, as previously mentioned, to provide a method and a device for the mechanical regulation of increased venous return (normalization) in patients with congestive heart failure; and it is based on the use of a catheter carrying an adjustable inflatable balloon, exhibiting eight (8) external slots. Said catheter and the balloon are percutaneously inserted, via left subclavian vein, continuing its pass through the right atrium and carried to the proximal portion of the inferior vena cava, in which it is anchored to the right sidewall, so that the balloon stays very close to the inferior vena cava outlet, in which the inspiratory collapse is maximal. After that, the balloon is inflated to a point to be determined for each patient, according to the needs of occlusion of said vein. The inflated balloon produces an instant and cyclical occlusion, according to the continuous succession of inspiratory collapses and expirations, thereby providing a flow regulation that runs from the inferior vena cava into the right atrium.

In this way, the load conditions of the right atrium, right ventricle and left ventricle are decreased. This situation is repeated in each inspiration (breath-in), preventing an increase of the flow rate that normally occurs in each inspiration, reducing also the flow rate and the filling pressure at left and right ventricles.

As a result of this normalization of venous return, there is a decrease of pulmonary congestion on the diastolic diameters of both ventricles and an improvement in the left ventricular ejection.

This model of instantaneous and dynamic regulation of the flow has the advantage that the balloon can be easily implanted by an expert, it is possible to modify and adjust it in situ without difficulty, in order to obtain the expected results;

and no external power generation is required to operate, since the flow regulation (normalization) is supported by the physiology of the patients when breathing in. Additionally, the said device can be removed without difficulties when required, by simply emptying the content of the balloon from the outside.

The operating mode of the method proposed by this Inventor to regulate the balloon and obtain the appropriate regulatory effect in each case or situation can be explained, in a general form, through the Examples that follow and then through the corresponding illustrative figures attached below:

Example 1

After localizing the patient's inferior vena cava by way of 2D echocardiography, in sub-costal position, in long axis view, its diameter should be measured during expiration (e.g., 2cm). The collapse is measured during patient inspiration (breath in), normally in the range of 50%, that is, 1cm diameter reduction for the said case.

Under these conditions, the balloon has to be inflated up to 1cm to complete 100% occlusion, when inspiration takes place (breath-in.)

Example 2

In the case that the inferior vena cava measures 2cm and the inspiratory collapse is 40%, the diameter of the vessel decreases to 1.2cm; therefore, the balloon should be inflated to that same measurement to obtain the desired occlusion of 100% during inspiration, thus achieving a dynamic flow regulation.

At the next stage of expiration, the inferior vena cava returns to its normal diameter, allowing venous return through the remaining area.

DESCRIPTION OF THE DRAWINGS

FIG. 1 is a schematic view of the device that includes an inflatable balloon with amplified details of this element at the distal end of the catheter, wherein A is a longitudinal sectional view; B is a cross-sectional view; C is a sagittal view, D IS an amplified cross-sectional view of B, E IS a cross-sectional external view, and F is an external top view.

FIG. 2a is a demonstration of the device being implanted in a human body.

FIG. 3a is an enlarged view of the inferior vena cava in expiration condition with the balloon anchored to that vein.

FIG. 3b is a complementary view of FIG. 3a, which includes the human heart in the initial phase of treatment of heart failure (dilated heart).

FIG. 4a is a view similar to FIG. 2a, only to indicate the return of the vein to the condition of inspiration.

Figure 2B:
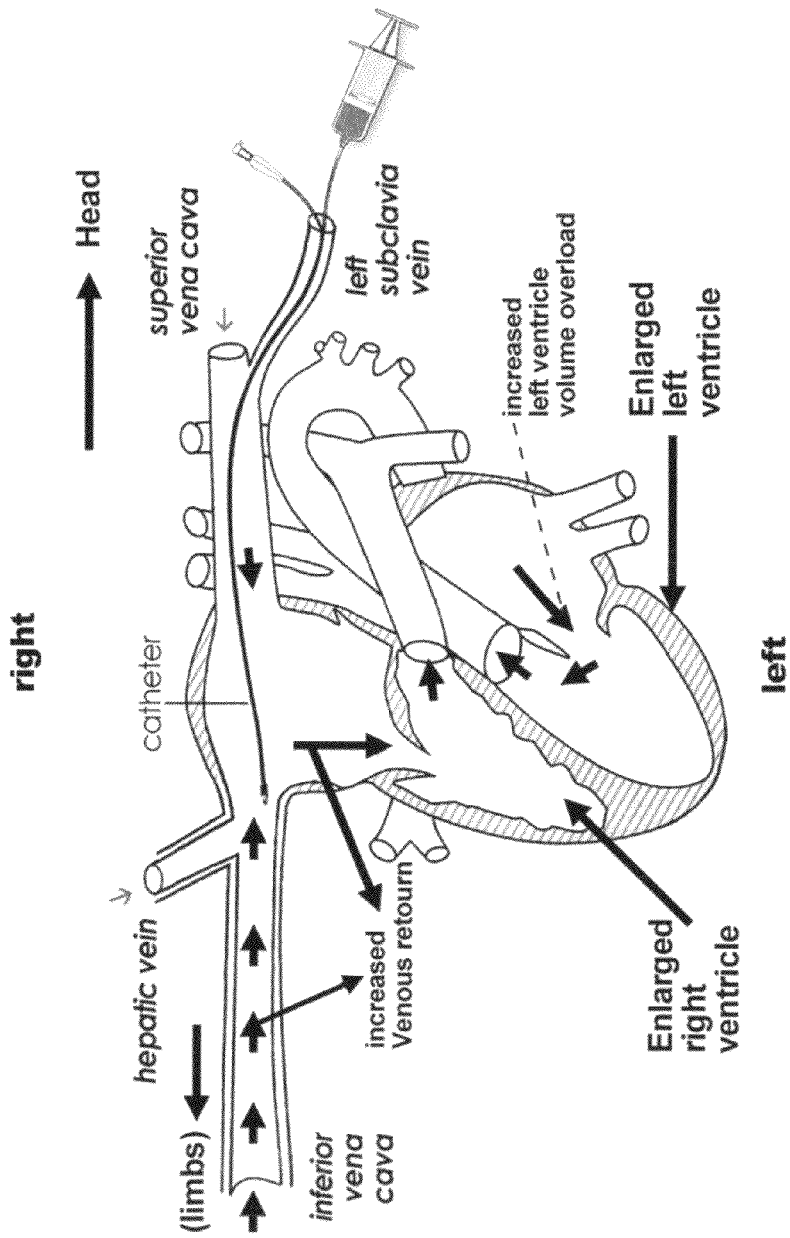
FIG. 2b is an enlarged view of the implantation of the device via the left subclavian vein through the superior vena cava until reaching the inferior vena cava.

Making a detailed description of the above described figures, it can be seen that FIG. 1 is comprised of a catheter (1) with a bifurcation (4) at its proximal end in which one of the branches leads to a cylindrical body (2) provided with an injection embolus (saline or glucose solution) into the interior of the balloon (5); and the other branch is provided with a jacket (3) to pass a probe and act on the distal retractable screw (6) for the anchoring of the catheter to the inferior vena cava. This retractable screw is a conventional element used since 1978 (Hurts, John Willis 1978), The Heart Text Book, page 701. The injection element (2) also features a non-return valve (7) to prevent the regression of the injected liquid into the balloon (5). Said balloon (5), as can be seen in the broken down detail A of FIG. 1, is egg-shaped to ease the flow of the bloodstream, further comprising of superficial slots parallel oriented to the longitudinal axis of the inferior vena cava.

The balloon (5) is intended to be inflated with a saline or glucose solution through the catheter in a range from 1 to 2 cm, in its greater diameter, depending on the patient needs. The wall of the balloon has a thickness of 1 mm covered by 8 slots of 0.5 mm in depth and 1 mm in width. The purpose of these slots is to act as relief of the venous return in the event of a total and prolonged occlusion of the inferior vena cava due to physiological conditions, such as coughing, laughing and evacuating (going to the toilet, etc.)

FIGS. 3a, 3b, 4a and 4b schematically show how the proposed method of the invention operates, assuming a patient with congestive heart failure. In FIG. 3 is seen a portion of the inferior vena cava corresponding to the confluence zone of said vena cava with the hepatic vein, where said vena cava is at the stage of expiration and at a diameter of 2cm. The balloon (5) (diameter=1cm) previously inserted in the vena cava, is near the outlet of the hepatic veins, THE area of major inspiratory collapse.

In the expiration condition, it can be seen that the flow of the bloodstream is essentially affected by minimal restriction.

FIG. 3b is a view of the whole device, including the anatomy of the human heart at the initial stage of the treatment, where the dilated heart due to congestive heart failure (CHF) can be seen.

Figure 4B:
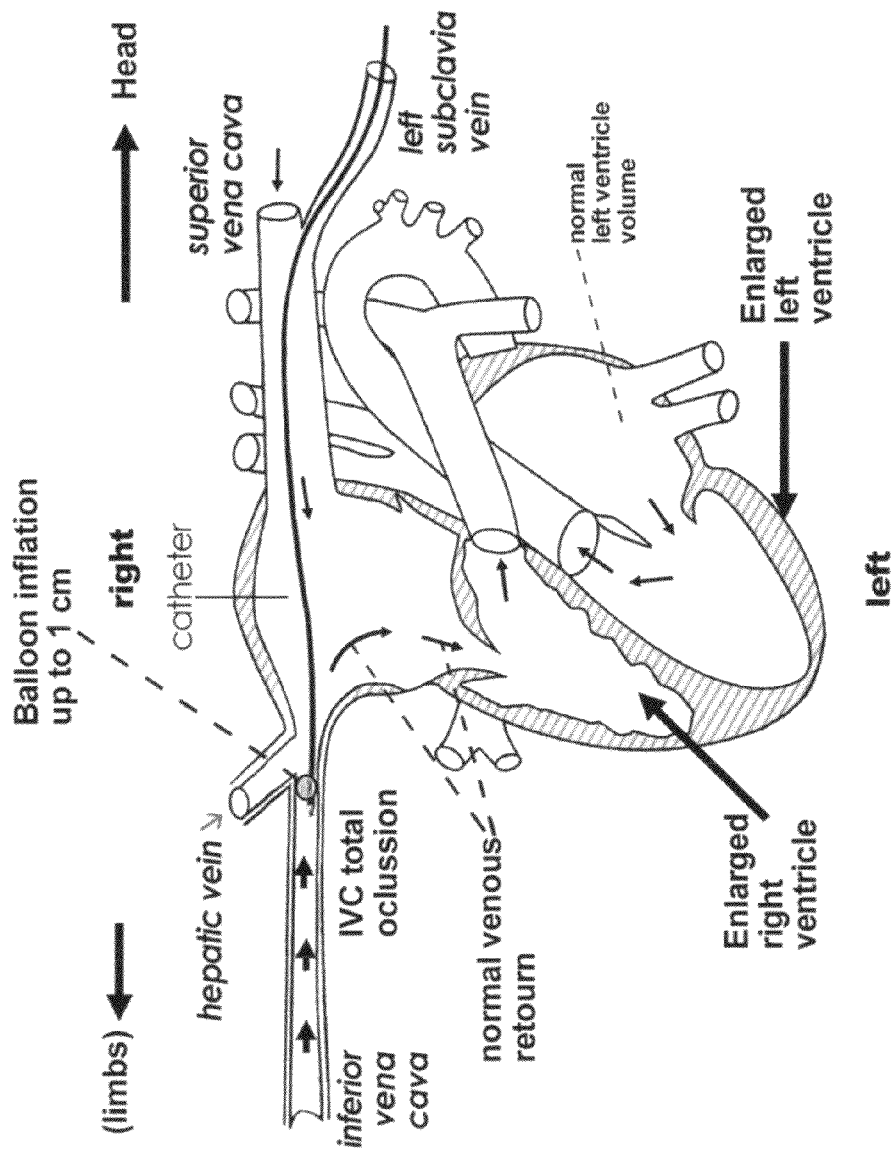
FIG. 4b is a complementary view of FIG. 4a that includes the human heart in the initial phase of treatment (dilated heart).

It can be observed in FIG. 4a how the balloon (5) operates (diameter=1cm) during the inspiration phase. The collapsing or reduction of the diameter of the inferior vena cava (1cm) now reaches the same diameter of the balloon, producing total occlusion of the vessel (which is the intended purpose) for an approximate time of 1 second (duration of the inspiratory collapse.) After this period, the inferior vena cava returns to its expiration phase, allowing blood flow again, as illustrated in FIGS. 3a and 4a; therefore, the venous return decreases due to the instant reduction of the flow, thereby decreasing the filling pressure at the right and left ventricles, which effects were previously explained. FIG. 4b is a view of the complete device including the anatomy of the human heart in the initial phase of the treatment in which a dilated heart with heart failure is shown.

Figure 5:
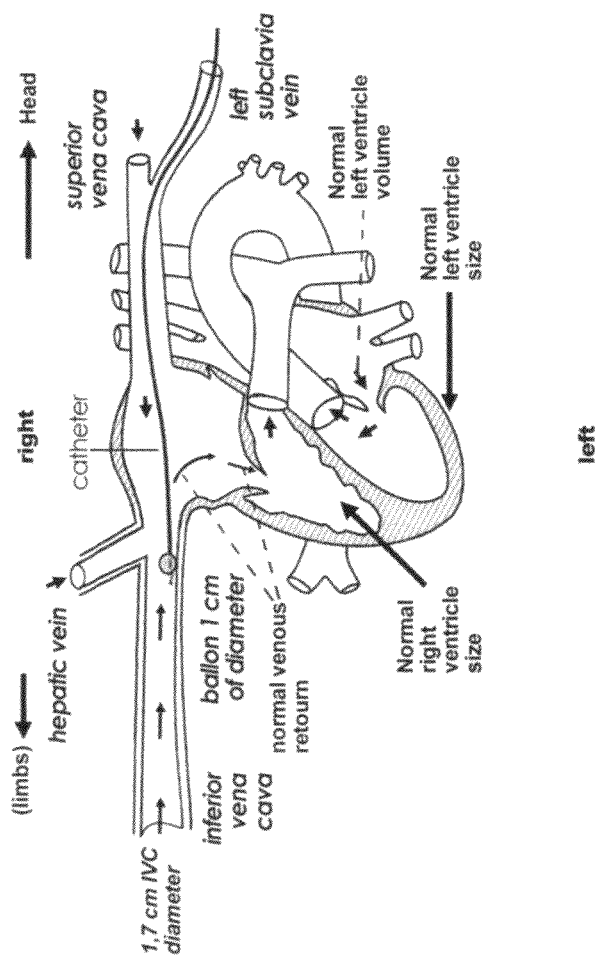
FIG. 5 is a view of the device implanted in the human heart in the final phase of treatment, which shows that the heart reduces its size, which indicates the correction of the heart failure (normal size heart).

FIG. 5 shows the complete device, including the anatomy of the heart at the end of the treatment, which shows a reduction in heart size, after a period three months, at least, when the characteristic symptoms of the heart failure improve.

While preferred embodiments of the invention have been shown and described, various modifications and substitutions may be made thereto without departing from the spirit and scope of the invention. Other variations and modifications may suggest themselves to a person skilled in the relevant arts.

Accordingly, it is to be understood that the present invention has been described by way of illustration only, and this description should not be construed as limiting to the several claims appended hereto.

The invention claimed is:

1. A device, comprising:
a two-way catheter having a distal end;
an inflatable balloon detachably disposed at a distal end of the catheter, said balloon being:
made of a flexible material that expands to increase a volume of the balloon,
configured to remain expanded once detached, and
having an external surface comprising one or more slots distributed longitudinally about an axis; and
an anchoring element which anchors at least a portion of the device to a blood vessel.

2. A device according to claim 1, wherein the device comprises a non-return valve that prevents the regression of an injected liquid into the balloon.

3. A device according to claim 1, wherein the number of slots is 8.

4. A device according to claim 1, wherein the anchoring element comprises a retractable screw.

5. A device according to claim 4, comprising a bifurcation having branches at its proximal end in which one of the branches leads to a cylindrical body provided with an injection embolus into the interior of the balloon, and the other branch is provided with a jacket to pass a probe and act on the retractable screw for the anchoring of the catheter to the inferior vena cava.

6. A device according to claim 4, wherein the retractable screw is located at a distal end of the catheter device.

* * * * *